(12) United States Patent
Hong et al.

(10) Patent No.: US 12,220,276 B2
(45) Date of Patent: Feb. 11, 2025

(54) ULTRASONIC PROBE

(71) Applicant: SAMSUNG MEDISON CO., LTD., Hongcheon-gun Gangwon-do (KR)

(72) Inventors: Minki Hong, Seongnam-si (KR); Jinho Gu, Seongnam-si (KR)

(73) Assignee: SAMSUNG MEDISON CO., LTD., Gangwon-Do (KR)

( * ) Notice: Subject to any disclaimer, the term of this patent is extended or adjusted under 35 U.S.C. 154(b) by 228 days.

(21) Appl. No.: 17/796,123

(22) PCT Filed: Feb. 12, 2020

(86) PCT No.: PCT/KR2020/001936
§ 371 (c)(1),
(2) Date: Jul. 28, 2022

(87) PCT Pub. No.: WO2021/157769
PCT Pub. Date: Aug. 12, 2021

(65) Prior Publication Data
US 2023/0118324 A1    Apr. 20, 2023

(30) Foreign Application Priority Data
Feb. 3, 2020    (KR) .......................... 10-2020-0012447

(51) Int. Cl.
*A61B 8/00*    (2006.01)
*G01N 29/28*    (2006.01)
(Continued)

(52) U.S. Cl.
CPC .......... *A61B 8/4461* (2013.01); *A61B 8/4422* (2013.01); *A61B 8/4483* (2013.01);
(Continued)

(58) Field of Classification Search
CPC ... A61B 8/4461; A61B 8/4422; A61B 8/4483; G10K 11/004; G01N 29/28; G01N 2291/0421; G01N 2291/044; G01S 7/521
(Continued)

(56) References Cited

U.S. PATENT DOCUMENTS 10,456,487 B2 * 10/2019 Bilenko .................... A61L 2/10
2016/0235305 A1 * 8/2016 Wang ................... A61B 5/0873
(Continued)

FOREIGN PATENT DOCUMENTS

CN    202342071 U  *  7/2012
CN    204318792 U  *  5/2015
(Continued)

OTHER PUBLICATIONS

Kac et al., Evaluation of a new disinfection procedure for ultrasound probes using ultraviolet light, Journal of Hospital Infection (2007) 65, 163-168 (Year: 2007).*
(Continued)

*Primary Examiner* — Stephanie E Bloss
*Assistant Examiner* — Kevin C Butler
(74) *Attorney, Agent, or Firm* — Morgan, Lewis & Bockius LLP (57) ABSTRACT

An ultrasonic probe is provided. The ultrasonic probe comprises: a case; a transducer which is arranged in the case and which converts electrical signals into ultrasonic waves; an acoustic lens which is arranged on the transducer and which causes the ultrasonic waves to converge in one area of a subject; and a plurality of light-emitting elements which are arranged in the case and which emit light in order to sterilize the external surface of the acoustic lens.

12 Claims, 7 Drawing Sheets

(51) Int. Cl.
*G01S 7/521* (2006.01)
*G10K 11/04* (2006.01)

(52) U.S. Cl.
CPC ..... *G01N 29/28* (2013.01); *G01N 2291/0421* (2013.01); *G01N 2291/044* (2013.01); *G01S 7/521* (2013.01); *G10K 11/04* (2013.01)

(58) Field of Classification Search
USPC .......................................................... 73/632
See application file for complete search history.

(56) References Cited

U.S. PATENT DOCUMENTS

| | | | |
|---|---|---|---|
| 2017/0042662 A1 | 2/2017 | Kubiak | |
| 2017/0296142 A1* | 10/2017 | Wodecki | A61B 8/4433 |
| 2018/0161004 A1* | 6/2018 | Son | A61B 8/4411 |
| 2018/0280555 A1* | 10/2018 | Bilenko | A61B 7/02 |
| 2019/0167230 A1* | 6/2019 | Cho | A61B 8/4444 |
| 2019/0239853 A1* | 8/2019 | Lee | G01S 15/894 |
| 2021/0153638 A1 | 5/2021 | Jeong et al. | |
| 2023/0118324 A1* | 4/2023 | Hong | A61B 8/4444 73/632 |
| 2023/0301626 A1* | 9/2023 | Howell | A61B 8/4254 |
| 2023/0338006 A1* | 10/2023 | B | A61B 8/4281 |

FOREIGN PATENT DOCUMENTS

| | | | | |
|---|---|---|---|---|
| CN | 106308727 A | * | 1/2017 | |
| CN | 109758179 A | * | 5/2019 | |
| CN | 215688006 U | * | 2/2022 | |
| CN | 116784875 A | * | 9/2023 | A61B 8/4254 |
| CN | 220695279 U | * | 4/2024 | A61B 8/4254 |
| EP | 3520701 A1 | * | 8/2019 | A61B 8/12 |
| JP | H05-31157 A | | 2/1993 | |
| JP | 2001299758 A | * | 10/2001 | |
| JP | 2006055236 A | * | 3/2006 | A61B 5/0073 |
| JP | 2008-178518 A | | 8/2009 | |
| JP | 2011-200374 A | | 10/2011 | |
| JP | 5189770 B2 | * | 4/2013 | |
| KR | 10-2009-0050723 A | | 5/2009 | |
| KR | 20090050723 A | * | 5/2009 | A61B 8/00 |
| KR | 10-2014-0003473 A | | 1/2014 | |
| KR | 20140003473 A | * | 6/2014 | A61B 8/00 |
| KR | 102107730 B1 | * | 7/2015 | A61B 8/00 |
| KR | 10-1848623 B1 | | 4/2018 | |
| KR | 20210098653 A | * | 8/2021 | A61B 8/4422 |
| KR | 20210153638 A | * | 12/2021 | A61B 5/00 |
| KR | 20220141507 A | * | 10/2022 | A61B 1/00 |
| WO | WO-2010080991 A2 | * | 7/2010 | A61B 5/0062 |
| WO | 2012/083023 A1 | | 6/2012 | |
| WO | WO-2021157769 A1 | * | 8/2021 | A61B 8/4422 |

OTHER PUBLICATIONS

Campbell et al., Medical Ultrasound Disinfection and Hygiene Practices: WFUMB Global Survey Results, 2018 World Federation for Ultrasound in Medicine & Biology, vol. 45, No. 2 pp. 344-352, 2019 (Year: 2019).*
Morriston Hospital Hepatitis B death: Lessons learned, says ABM health board—BBC News, https://www.bbc.com/news/uk-wales-south-west-wales-17624476, Apr. 5, 2022 (Year: 2022).*
International Search Report and Written Opinion dated Oct. 28, 2020 issued in International Patent Application No. PCT/KR2020/001936 (with English translation).
"Morriston Hospital hepatitis B death: Lessons learned, says ABM health board," BBC, Apr. 5, 2022, URL: https://www.bbc.com/news/uk-wales-south-west-wales-17624476.
S. C. Westerway, et al., "Medical Ultrasound Disinfection and Hygiene Practices: WFUMB Global Survey Results," ScienceDirect, vol. 45, Issue 2, pp. 344-352, Feb. 2019.
European Notice of Allowance dated Feb. 16, 2024 issued in European Patent Application No. 20917861.5.
G. Kac et al., "Evaluation of a new disinfection procedure for ultrasound probes using ultraviolet light," Journal of Hospital Infection, Elsevier, Amsterdam, NL, vol. 65, No. 2, Jan. 13, 2007, pp. 163-168, XP005761585.
The Extended European Search Report dated May 12, 2023 issued in European Patent Application No. 20917861.5.
European Notice of Allowance dated May 13, 2024 issued in European Patent Application No. 20917861.5.
Korean Office Action dated Aug. 24, 2024 issued in Korean Patent Application No. 10-2020-0012447 (with English translation).

* cited by examiner

| Comparison of Mercury UV Lamp vs UV-C LED ||||| 
|---|---|---|---|---|
| | Environment | Durability | Lifetime | Size |
| Mercury Lamp | Including Mercury | Damage Risk | 2,000~10,000 Hours | > 10cm |
| UV-C LED | Mercury Free | Excellent Durability | 10,000~50,000 Hours | < 1cm |

FIG. 5

| Microorganism | Drive Current (mA) | Setup Distance | Module Wavelength | Treatment Time (secs) | Untreated Control (CFU/plate) | After Treatment (CFU/plate) | Log Reduction | Efficiency(%) |
|---|---|---|---|---|---|---|---|---|
| Escherichia coli ATCC 25922 | 100 | 10mm | 278nm | 20 | $1.86 \times 10^6$ | <1 | ≥3.00 | >99.99 |
| | 350 | 10mm | 278nm | 20 | $1.53 \times 10^6$ | <1 | ≥3.00 | >99.99 |
| | 350 | 100mm | 278nm | 20 | $1.29 \times 10^6$ | <1 | ≥3.00 | >99.99 |
| Staphylococcus Aureu (MRSA) ATCC 6538 | 350 | 10mm | 278nm | 20 | $1.49 \times 10^6$ | <1 | ≥3.00 | >99.99 |
| | 350 | 10mm | 278nm | 10 | $1.50 \times 10^6$ | <1 | ≥3.00 | >99.99 |
| | 350 | 10mm | 282nm | 20 | $1.13 \times 10^6$ | <1 | ≥3.00 | >99.99 |

ULTRASONIC PROBE

TECHNICAL FIELD

The present invention relates to an ultrasonic probe, and more particularly, to an ultrasonic probe having a sterilizing function.

BACKGROUND ART

An ultrasonic diagnostic apparatus is an apparatus which irradiates ultrasonic waves toward a target point inside a subject from the surface of the subject, and receives the ultrasonic waves (echo ultrasonic waves) reflected from the target point so as to non-invasively obtain a tomographic image of soft tissue of the subject or an image of blood flow of the subject.

The ultrasonic diagnostic apparatus has a compact size and is cheaper, as compared to other medical imaging apparatuses, such as an X-ray diagnostic apparatus, a CT scanner (Computerized Tomography Scanner), an MRI (Magnetic Resonance Image), and a nuclear medicine diagnosis apparatus. Also, the ultrasonic diagnostic apparatus acquires an image regarding the interior of the subject in real time, and has a high safety level without radiation exposure. Thus, the ultrasonic diagnostic apparatus is widely used for heart diagnosis, celiac diagnosis, urinary diagnosis and obstetrical diagnosis.

The ultrasonic diagnosis apparatus includes an ultrasonic probe which transmits an ultrasonic signal to a subject and which receives a response signal reflected from the subject to acquire an ultrasonic image of the subject. In order to prevent infection caused by bacteria, and the like, it is necessary to periodically perform sterilization on the ultrasonic probe.

DETAILED DESCRIPTION OF INVENTION

Technical Problem

The present invention is conceived to solve the aforementioned problems. Accordingly, an object of the present invention is to provide an ultrasonic probe having a sterilizing function.

Technical Solution

In accordance with an aspect of the present invention, there is provided an ultrasonic probe including: a case; a transducer arranged in the case, the transducer converting electrical signals into ultrasonic waves; an acoustic lens arranged on the transducer, the acoustic lens causing the ultrasonic waves to converge in one area of a subject; and a plurality of light emitting elements arranged in the case, the plurality of light emitting elements emitting light to sterilize an external surface of the acoustic lens.

In addition, at least one of the plurality of light emitting elements may be in direct contact with the acoustic lens.

Also, at least one of the plurality of light emitting elements may be covered by the acoustic lens.

In addition, the light may sterilize the external surface of the acoustic lens while being transmitted through the acoustic lens.

In addition, at least one of the plurality of light emitting elements may emit light of a UV-C wavelength.

Also, at least one of the plurality of light emitting elements may be arranged more distant from a central axis of the ultrasonic probe than the transducer.

Also, the plurality of light emitting elements may be symmetrically arranged with respect to a central axis of the ultrasonic probe.

In addition, the ultrasonic probe may further include a support member arranged in the case, the support member supporting the plurality of light emitting elements.

In addition, the support member may include: a first area overlapping with the transducer; and a second area supporting the plurality of light emitting elements.

In addition, the second area may be inclined with respect to the first area.

Also, in the second area, the size of a cavity may become larger as becoming more distant from the first area.

In addition, the acoustic lens may be formed of a material having a transmission of the light, which is 50% or more.

Also, the acoustic lens may include at least one of PDMS (polydimethyl siloxane), octamethylcyclotetra siloxane, fluorine-polymer, a silicon material, RTV (Room Temperature Vulcanizing), silicon rubber, and polyurethane.

In addition, the plurality of light emitting elements may be arranged on an area not overlapping with an advancing path of the ultrasonic waves inside the case.

Also, the plurality of light emitting elements may emit the light in a state in which the transducer is inactivated.

Advantageous Effects

Since a light emitting element for emitting light for sterilization is provided in the ultrasonic probe, any separate apparatus for sterilization is not required.

MODE FOR THE INVENTION

Configurations illustrated in the embodiments and the drawings described in the present specification are only the preferred embodiments of the present invention, and thus it is to be understood that various modified examples, which may replace the embodiments and the drawings described in the present specification, are possible when filing the present application.

The terms used in the present specification are used for the purpose of describing the example embodiments, and not for the purpose of limiting and/or restricting the present invention. As used herein, the singular forms are intended to include the plural forms as well, unless the context clearly indicates otherwise.

It will be further understood that the terms "includes" and/or "including", when used in this specification, specify the presence of stated features, integers, steps, operations, elements, and/or components, but do not preclude the presence and/or addition of one or more other features, integers, steps, operations, elements, components, and/or groups thereof.

Hereinafter, exemplary embodiments are described in detail with reference to the accompanying drawings so that those skilled in the art may easily practice the present invention.

Figure 1:
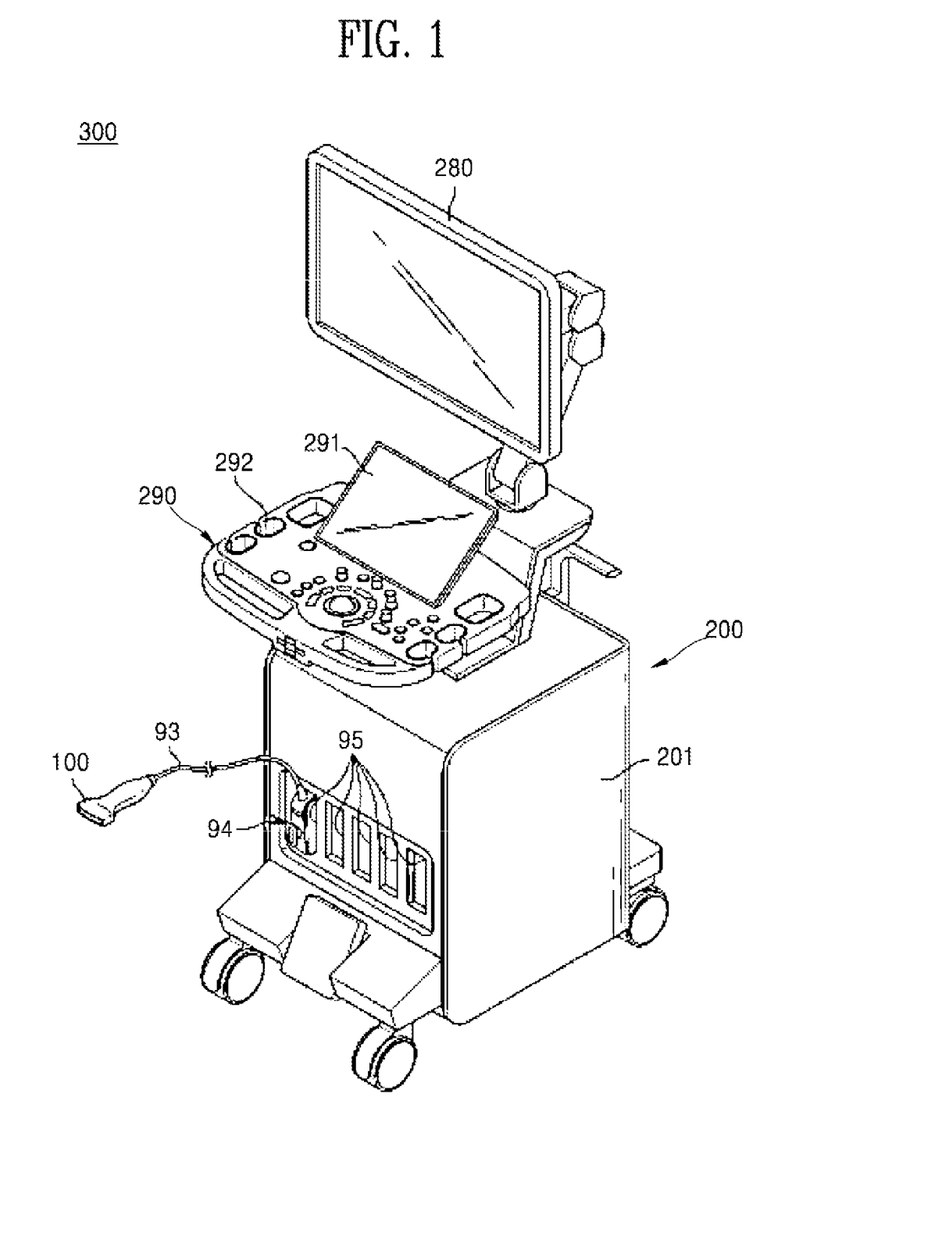
FIG. 1 is a perspective view illustrating an embodiment of an ultrasonic diagnostic apparatus including an ultrasonic probe in accordance with an embodiment of the present invention.

FIG. 1 is a perspective view illustrating an embodiment of an ultrasonic diagnostic apparatus 300 including an ultrasonic probe 100 in accordance with an embodiment of the present invention.

Referring to FIG. 1, the ultrasonic diagnostic apparatus 300 may include a main body 200, an input unit 290 which is input with a command for controlling the ultrasonic diagnostic apparatus 300 from a user, and a display 280 which outputs information received from the main body 200.

Specifically, the main body 200 may control overall operations of the ultrasonic diagnostic apparatus 300. Accordingly, various types of components for controlling overall operations of the ultrasonic probe 100 or the main body 200 may be provided, and the main body 200 and the ultrasonic probe 100 may communicate data with each other by using a connection cable 93 or a wireless communication module.

Also, the ultrasonic probe 100 and the main body 200 may be connected to communicate with each other by using the connection cable 93 as shown in FIG. 1. An electrical signal output from the ultrasonic probe 100 through the connection cable 93 may be transferred to the main body 200. In addition, a control command and the like, generated in the main body 200, may also be transferred to the ultrasonic probe 100 through the connection cable 93.

A connector 94 may be provided at one end of the connection cable 93. The connector 94 may be coupled to and separated from a port 95 provided at an exterior 201 of the main body 200. When the connector 94 is coupled to the port 95, the ultrasonic probe 100 and the main body 200 may be communicably connected to each other.

In addition, a probe holder 292 capable of allowing the ultrasonic probe 100 to be held thereby may be provided at one side surface of the main body 200. The probe holder 292 may be provided as many as a number of ultrasonic probes 100, and be attached to or detached from the main body 200. When the user does not use the ultrasonic probe 100, the ultrasonic probe 100 may be held and keep by the probe holder 292.

In addition, the main body 200 may receive an electrical signal output from the ultrasonic probe 100 and transfer an electrical signal generated in the main body 200 to the ultrasonic probe 100 through a wireless communication. In this case, a wireless communication module including an antenna and a wireless communication chip may be installed inside each of the ultrasonic probe 100 and the main body 200.

The wireless communication module may be a near field wireless communication module using at least one of Bluetooth low energy, IrDA (infrared data association), Wi-Fi, Wi-Fi Direct, UWB (Ultra-Wideband), and NFC (Near Field Communication), and be a wireless communication module which supports a 3GPP-based, 3GPP2-based or IEEE-based wireless communication network approved by the International Telecommunication Union (ITU).

The main body 200 may exchange data with a hospital server or another medical apparatus of a hospital, which connected thereto through a PACS (Picture Archiving and Communication System), through a communication unit. Also, the main body 200 may perform data communication according to a DICOM (Digital Imaging and Communications in Medicine) standard. However, the present invention is not limited thereto.

The display 280 may be coupled to the main body 200 and output various information received from the main body 200.

Specifically, the display 280 may display an ultrasonic image of a target part inside a subject. The ultrasonic image displayed on the display 280 may be a two-dimensional ultrasonic image, a three-dimensional ultrasonic image, or a Doppler image, and various ultrasonic images may be displayed according to an operation mode of the ultrasonic diagnostic apparatus 300.

In accordance with an embodiment, the ultrasonic image includes not only an Amplitude Mode (A-Mode) image, a Brightness Mode (B-mode) image, and a Motion Mode (M-Mode), but also a C (Color)-mode image and a D (Doppler)-mode image.

As used herein, the A-mode image means an ultrasonic image representing the intensity of an ultrasonic signal corresponding to an echo ultrasonic signal, the B-mode image means an ultrasonic image representing the intensity of the ultrasonic signal corresponding to the echo ultrasonic signal using brightness, and the M-mode image means an ultrasonic image representing motion of a subject at a specific position according to time. The D-mode image means an ultrasonic image representing a moving subject in the form of waveforms according to the Doppler Effect. The C-mode image means an ultrasonic image representing a moving subject in the form of color spectrums.

Therefore, the display 280 may be implemented as well-known various displays, such as a Cathode Ray Tube (CRT), an LCD (Liquid Crystal Display), an LED (Light Emitting Diode), a PDP (Plasma Display Panel), and an OLED (Organic Light Emitting Diode).

The input unit 290 may be variously implemented, such as a keyboard, a foot switch, a foot pedal, or the like.

For example, the keyboard may be implemented by hardware. The keyboard may include at least one of a switch, a key, a joystick, and a track ball. Alternatively, the keyboard may be implemented by software, such as a graphical user interface. In this case, the keyboard may be displayed through the display 280.

Meanwhile, when the display 280 is implemented as a touch screen type display, the display 280 may also serve as the input unit 290. That is, the main body 200 may receive various commands from the user through at least one of the display 280 and the input unit 290. In an embodiment, a display 291 shown FIG. 1 may perform both a display function and an input function.

The display 280 and the input unit 290 may be defined together as an input/output unit 270, in that the display 280 and the input unit 290 receive information from the user or transmit information to the user.

Figure 2:
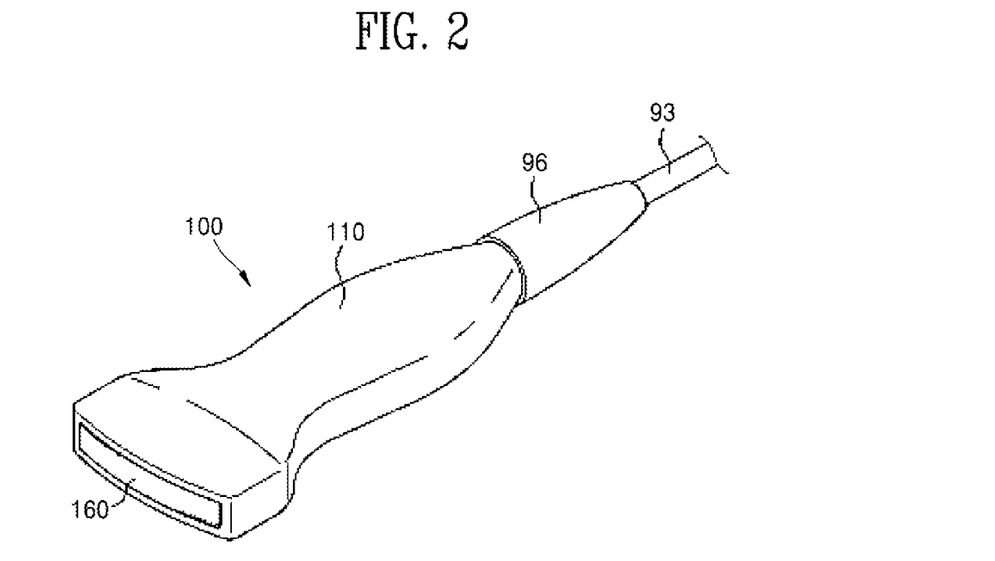
FIG. 2 is a perspective view of an ultrasonic probe in accordance with an embodiment of the present invention.

FIG. 2 is a perspective view of an ultrasonic probe 100 in accordance with an embodiment of the present invention.

Referring to FIG. 2, the ultrasonic probe 100 in accordance with the embodiment of the present invention includes a case 110 in which an ultrasonic transceiver, a transducer 120, and the like are accommodated, and a connection cable 93 which connects the ultrasonic transceiver and the main body 200 of the ultrasonic diagnostic apparatus 300 to each other.

An acoustic lens 160 (140) is disposed at the other end portion of the case 110, to which the connection cable 93 is not connected. A transducer 120 module disposed inside the case 110 may irradiate generated ultrasonic waves onto a subject through the acoustic lens 160 (140).

When an inspector uses the ultrasonic probe 100, the connection cable 93 may be rapidly bent or twisted at an end portion of the case 110 of the ultrasonic probe 100. When the connection cable 93 is rapidly bent or twisted, the connection cable 93 may be disconnected, or a jacket of the connection cable 93 may be damaged. In order to prevent the connection cable 93 from being rapidly bent or twisted at the end portion of the case 110 of the ultrasonic probe 100, the ultrasonic probe 100 may include a strain relief 96 provided to surround the connection cable 93 at the end portion of the case 110, at which the connection cable 93 is connected. That is, the strain relief 96 is provided at the outside of one end portion of the case 110 so as to prevent damage of the connection cable 93.

The strain relief 96 may be formed of a flexible material such that the connection cable 93 is gently bent. Although the strain relief 96 is formed of the flexible material, the stain relief 96 is to have hardness to a certain degree so as to prevent rapid bending of the cable. Therefore, the stain relief 96 may preferably have a structure which is easily curved toward one side or a structure capable of being bent in multistage while having a certain hardness.

In FIGS. 1 and 2, it is illustrated that the ultrasonic probe 100 is connected to the main body through the connection cable. However, the present invention is not limited thereto. The ultrasonic probe 100 may be wirelessly connected to the main body.

Figure 3:
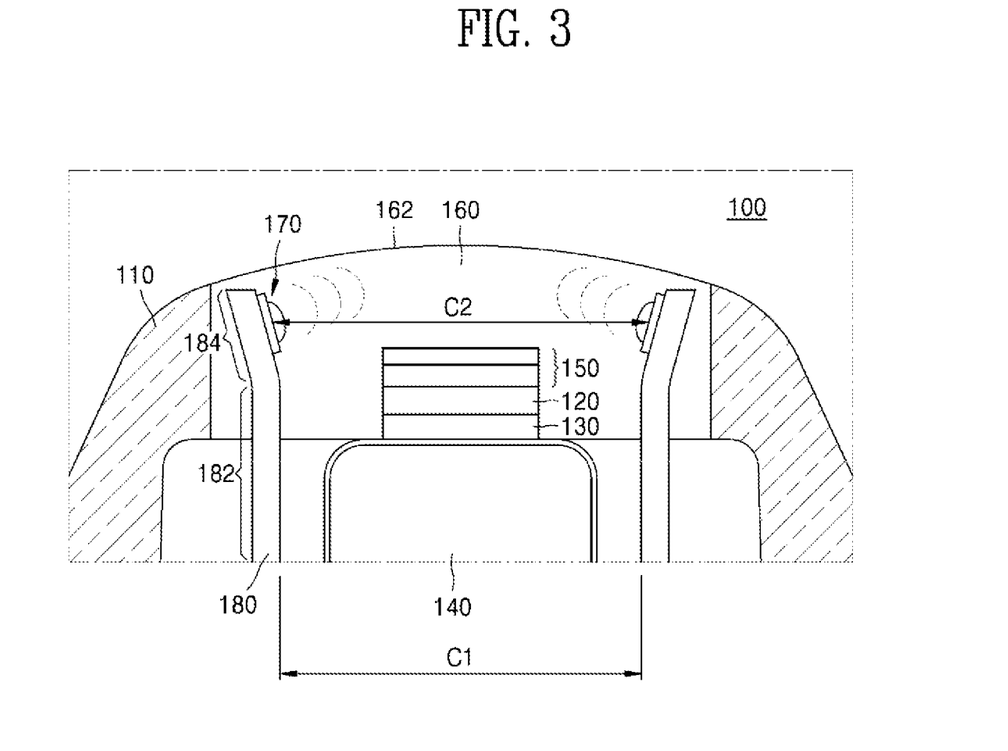
FIG. 3 is a partial cut-away perspective view schematically illustrating an internal configuration of an ultrasonic probe in accordance with an embodiment of the present invention.

FIG. 3 is a partial cut-away perspective view schematically illustrating an internal configuration of an ultrasonic probe 100 in accordance with an embodiment of the present invention.

As shown in FIG. 3, the ultrasonic probe 100 may include a case 110 forming a body, a transducer 120 which converts between an electrical signal and an acoustic signal, e.g., an ultrasonic wave, a dematching member which amplifies an ultrasonic wave, a sound absorbing member 140 which absorbs an ultrasonic wave transmitted in the opposite direction of a subject, a matching member 150 which matches an acoustic impedance of an ultrasonic wave generated in the transducer 120 to an acoustic impedance of the subject, and an acoustic lens 160 which focuses ultrasonic waves.

The transducer 120 is formed as at least one piezoelectric element which converts between an electrical signal and an ultrasonic wave while vibrating. The piezoelectric element may be formed by dividing a piezoelectric material into a plurality of piezoelectric elements. For example, the piezoelectric element may be manufactured by performing dicing processing on the piezoelectric material formed long in a length direction. However, the manufacturing of the piezoelectric element by dividing the piezoelectric material into the plurality of piezoelectric elements is not limited to the above-described method, and the piezoelectric element may be manufactured in various methods in addition to a method of a plurality of piezoelectric elements by pressing the piezoelectric material, using a metal mold, and the like. The above-described piezoelectric material may be a piezoelectric ceramic which may cause a piezo phenomenon, a single crystalline, a complex piezoelectric material obtained by combining the material with a polymer, or the like.

The transducer 120 may be implemented as a capacitive micromachined ultrasonic transducer (cMUT) which converts between an ultrasonic wave and an electrical signal according to a capacitance change, a magnetic micromachined ultrasonic transducer (mMUT) which converts between an ultrasonic wave and an electrical signal according to an magnetic-field change, an optical ultrasonic detector which converts between an ultrasonic wave and an electrical signal according to an optical-characteristic change, in addition to a transducer 120 which converts between an ultrasonic wave and an electrical signal according to a pressure change.

The dematching member 130 which reflects an incident ultrasonic wave may be further disposed on a bottom surface of the transducer 120. The dematching member 130 may reflect an ultrasonic wave transmitted in the opposite direction of a subject. The above-described dematching member 130 may improve acoustic characteristics of ultrasonic waves. The dematching member 130 does not substantially convert between an electrical signal and an ultrasonic wave, but allows an ultrasonic wave to be generated in the transducer 120 by vibrating together with the transducer 120. Hence, the dematching member 130 may be a partial configuration of the transducer 120.

An acoustic impedance of the dematching member 130 may be greater than or equal to an acoustic impedance of the transducer 120. For example, the acoustic impedance of the dematching member 130 may be twice of the acoustic impedance of the transducer 120. Therefore, an ultrasonic wave incident onto the dematching member 130 may be symmetrically reflected. The above-described dematching member 130 may be formed of a material such as tungsten carbide. The dematching member 130 may be disposed on the bottom surface of the transducer 120.

The sound absorbing member 140 which is transmitted toward the back of the transducer 120 to absorb an ultrasonic wave not directly used for inspection, diagnosis or the like may be further disposed at a rear surface of the transducer 120.

The matching member 150 which allows an acoustic impedance of an ultrasonic wave generated in the transducer 120 to come close to an acoustic impedance of a subject by stepwisely changing the acoustic impedance of the ultrasonic wave may be further disposed at a front surface of the transducer 120. The front surface of the transducer 120 may mean a surface closest to a subject to be inspected among surfaces of the transducer 120 while an ultrasonic wave is generated toward the subject to be inspected, and the rear surface may mean the opposite surface of the front surface.

The matching member 150 may be formed long along the front surface of the transducer 120. However, the present invention is not limited thereto, and the matching member 150 may be partially formed. Also, the matching member 150 is formed in a single layer, but may have a multi-layer structure.

The acoustic lens 160 which focuses ultrasonic waves generated in the transducer 120 may be further disposed at the front surface of the transducer 120. The acoustic lens 160 may be formed of a material having an acoustic impedance close to a subject. In addition, the center of the acoustic lens 160 may be convex or flat. The acoustic lens 160 may have various shapes according to the design of a designer.

The ultrasonic probe 100 may further include a plurality of light emitting elements 170 which irradiate light onto an external surface 162 of the acoustic lens 160. The light emitting element 170 may irradiate light for sterilization to eliminate bacteria which may be generated due to continuous use of the ultrasonic probe 100. The light emitting element 170 may emit ultraviolet light to the acoustic lens 160. For example, the light emitting element 170 may be a UV light emitting diode (LED).

When the ultrasonic probe 100 is not sterilized after ultrasonic scanning of the ultrasonic probe 100, the ultrasonic probe 100 may be exposed to a risk of bacterium infection. When the ultrasonic probe 100 is sterilized by using a separate sterilizing apparatus, there is an inconvenience in use. In the ultrasonic probe 100 in accordance with the embodiment of the present invention, since the light emitting element 170 is disposed inside the case 110, the external surface 162 of the acoustic lens 160 is automatically sterilized, so that secondary bacterium infection can be prevented.

Figure 4:
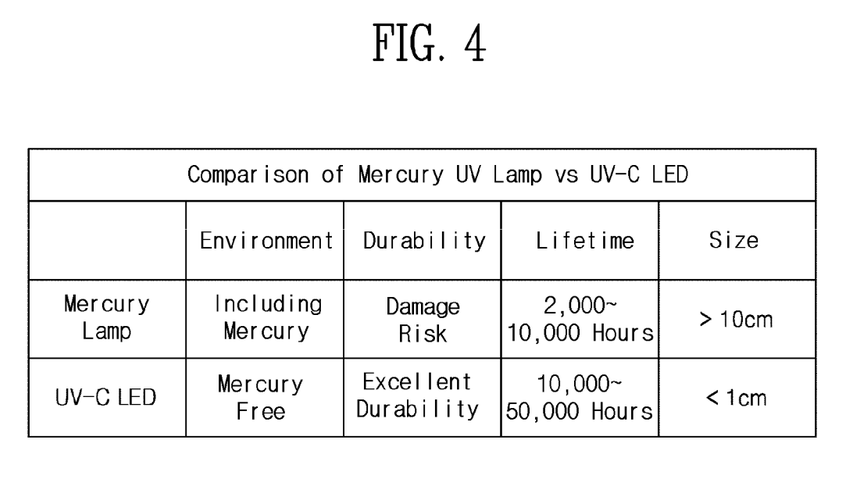
FIG. 4 is a view comparing characteristics of a UV lamp and a UV LED.

FIG. 4 is a view comparing characteristics of a UV lamp and a UV LED. As shown in FIG. 4, the UV LED does not contain mercury which may destruct an environment and has high durability, as compared with a mercury UV lamp. The UV LED has a remarkably long lifetime and a small size, as compared with the mercury UV lamp. In addition, the UV lamp has large power consumption and uses a high voltage in lighting, and hence, a problem of explosion and safety may occur. On the other hand, in the case of the UV LED, there is no problem of explosion and a safety zone since a driving voltage is a few V, and power consumption is low since a driving current is a few tens to a few hundreds of mA. Thus, the ultrasonic probe 100 in accordance with the embodiment of the present invention can use, as the light emitting element 170, the UV LED instead of the UV lamp.

Meanwhile, ultra violet (UV) light may be divided into a UV-A (315 to 400 nm), UB-B (285 to 315 nm), and UV-C (200 to 280 nm) wavelengths according to wavelengths thereof. Since a sterilization effect becomes larger as the wavelength becomes shorter, the light emitting element 170 in accordance with the embodiment of the present invention may be implemented as a UV-C LED which irradiates light of the UV-C wavelength. The above-described UV-C LED can exhibit an instantaneous sterilization effect. The light emitting element 170 in accordance with the embodiment of the present invention may emit light of the UV-C wavelength at a driving current in a range of 100 mA to 350 mA within 20 seconds.

Figure 5:
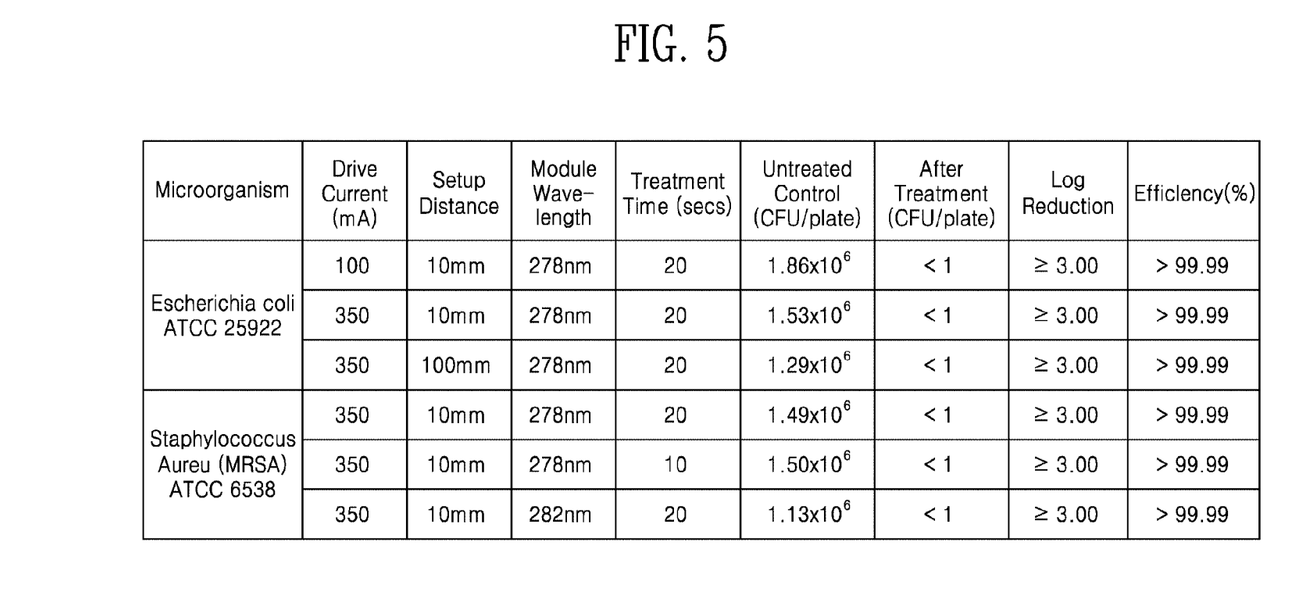
FIG. 5 is a reference view illustrating a sterilization effect using a UV-C LED in accordance with an embodiment of the present invention.

FIG. 5 is a reference view illustrating a sterilization effect using the UV-C LED in accordance with an embodiment of the present invention. The UV LED of which wavelength length is about 276 to 283 nm irradiated light onto a bacteria sample distant by 10 mm therefrom. The bacteria sample was *Escherichia coli* and staphylococcus (MRSA). As a result obtained by irradiating light of a UV-C wavelength, it can be seen that bacteria of 99.9% has been sterilized within 20 seconds as shown in FIG. 5. In addition, the LED may perform a sterilizing function while being little influenced by a peripheral temperature. Besides, the LED is advantageous in miniaturization and integration, and an array arrangement may also be easily manufactured. For example, each light emitting element 170 may have a size of about 10 mm or less.

The light of the UV-C wave, which the above-described light emitting element 170 emits, has the sterilizing function, but may damage a component of the ultrasonic probe 100. Therefore, the light emitted from the light emitting element 170 may be preferably minimized to be irradiated onto the transducer 120 of the ultrasonic probe 100 or a circuit module.

The light emitting element 170 may be disposed to be spaced apart from the transducer 120. The light emitting element 170 is disposed to be spatially spaced apart from the transducer 120, so that irradiation of light onto the transducer 120 can be minimized. For example, a partial area of the acoustic lens 100 may be disposed between the light emitting element 170 and the transducer 120.

In addition, the ultrasonic probe 100 may further include a support member 180 which supports the light emitting element 170. The support member 180 may have a shell shape which forms a space for accommodating the sound absorbing member 140, a transistor, a matching layer, and the like. The support member 180 may include a first area 182 in which the sectional size of a cavity C1 is constant and a second area 184 in which the sectional size of a cavity C2 becomes larger as becoming more distant from the first area 182.

The sound absorbing member 140 and the transducer 120 may be disposed in a space formed by the above-described first area 182, and the acoustic lens 160 may be disposed in an internal space formed by the second area 184. The second area 184 may be disposed more distant from the sound absorbing member 140 than the transducer 120. In addition, the light emitting element 170 may be disposed in the second area 184 of the support member 180. Thus, the amount of light irradiated onto the transducer 120 can be reduced, and light can be uniformly irradiated onto a surface of the acoustic lens 160.

Meanwhile, a slope degree of the second area 184 with respect to the first area 182 may be determined by a relative position between the light emitting element 170 and the transducer 120, an optical angle of the light emitting element 170, and the like. For example, when the optical angle of the light emitting element 170 is about 140 degrees, a slope angle of the second area 184 with respect to the first area 182 may be about 70 degrees. Therefore, light emitted from the light emitting element 170 may not advance toward the rear of the ultrasonic probe 100.

The above-described element 170 may be disposed not to overlap with an advancing path of an ultrasonic wave released from the transducer 120. For example, the light emitting element 170 may be disposed more distant from a central axis of the ultrasonic probe 100 than the transducer 120. Therefore, the light emitting element 170 may not interrupt the advancing path of the ultrasonic wave released from the transducer 120. Also, the plurality of light emitting elements 170 may be symmetrically arranged with respect to the central axis of the ultrasonic probe 100.

Meanwhile, the light emitting element 170 may be disposed to be in direct contact with the acoustic lens 160. The acoustic lens 160 may be formed by performing mold processing on a material such as silicon rubber after an ultrasonic module 420 including the transducer 120 and the light emitting element 170 are mounted in the case 110.

Therefore, the light emitting element 170 may be covered by the acoustic lens 160. Since the light emitting element 170 is in direct contact with the acoustic lens 160, light emitted from the light emitting element 170 may be transmitted through the acoustic lens 160 while reducing distribution and then reach the external surface 162 of the acoustic lens 160.

The acoustic lens 160 in accordance with the embodiment of the present invention may be formed of a material which focuses ultrasonic waves and has a high transmission with respect to light emitted from the light emitting element 170. The above-described acoustic lens 160 may be formed of a material of which transmission with respect to the light emitted from the light emitting element 170 is 50% or more. For example, the acoustic lens 160 may include at least one of PDMS (polydimethyl siloxane), octamethylcyclotetra siloxane, flurorine-polymer, a silicon material, RTV (Room Temperature Vulcanizing), silicon rubber, and polyurethane.

Figure 6:
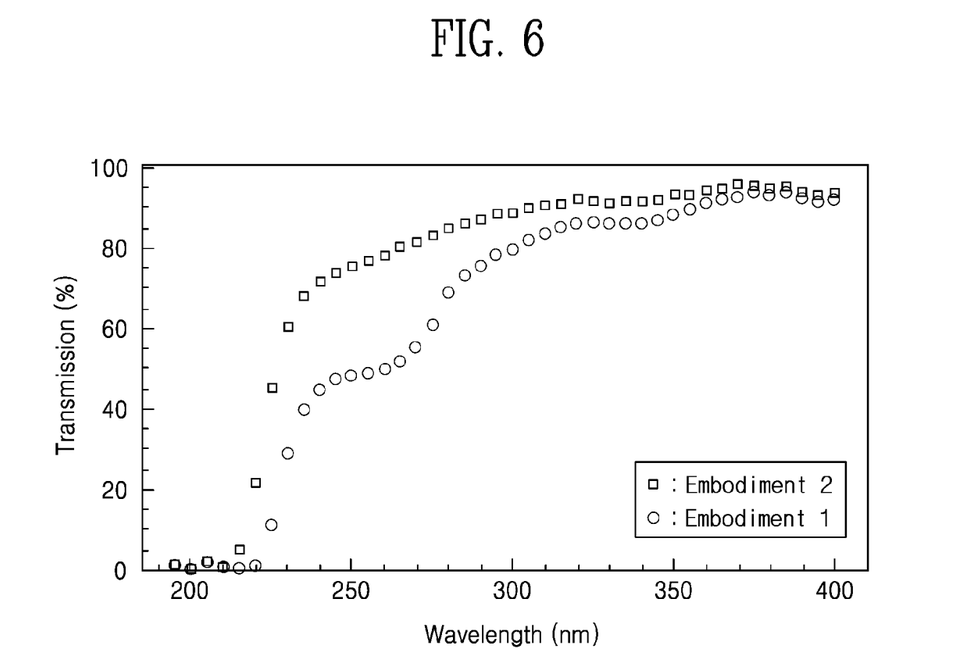
FIG. 6 is a view illustrating transmissions of an acoustic lens according to wavelengths in accordance with an embodiment of the present invention.

FIG. 6 is a view illustrating transmissions of the acoustic lens 160 according to wavelengths in accordance with an embodiment of the present invention. Silicon rubber was used as a material of the acoustic lens 160. In Embodiment 1, a thickness of the silicon rubber was about 1.3 mm. In Embodiment 2, a thickness of the silicon rubber was about 3.3 mm. As shown in FIG. 6, it can be seen that, the transmission of light becomes larger as the thickness becomes thinner, but even light of a wavelength of about 275 nm has a transmission of 50% or more. This means that, although a lower end of the acoustic lens 160, i.e., the light emitting element 170 is disposed in the probe, light can sterilize the surface of the acoustic lens 160 while being transmitted through the acoustic lens 160.

Meanwhile, a portion of light emitted from the light emitting element 170 may be converted into heat while the light passes through the acoustic lens 160. The above-described heat may change a characteristic of the acoustic lens 160, and hence the light emitting element 170 may preferably emit light for only a short time. For example, the light emitting element 170 may irradiate light within only about 20 seconds, thereby preventing degradation of the acoustic lens 160.

Figure 7:
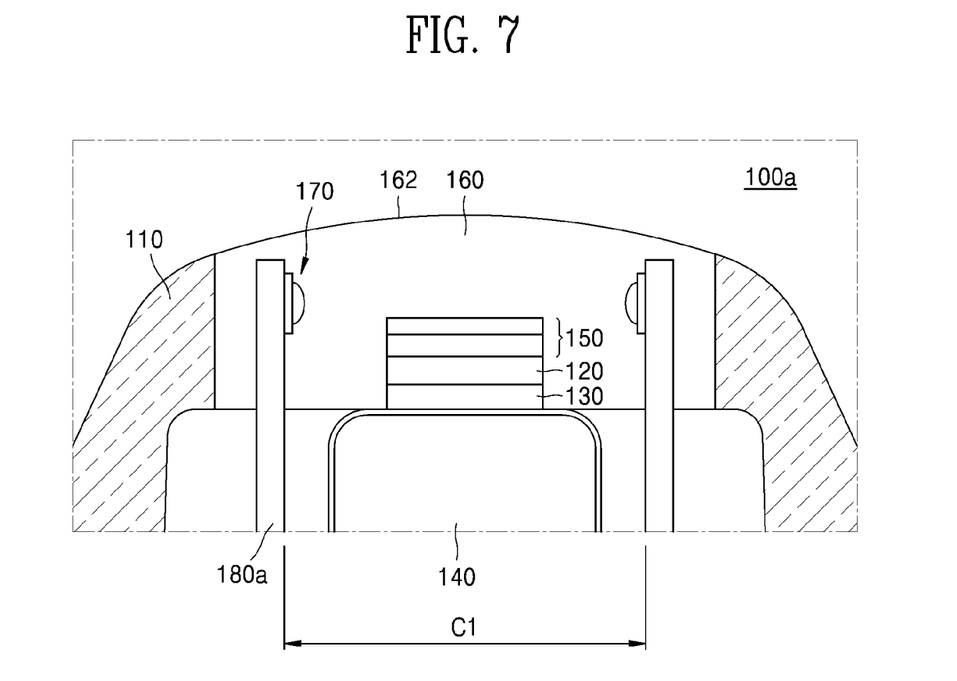
FIG. 7 is a view illustrating an ultrasonic probe in accordance with another embodiment of the present invention.

FIG. 7 is a view illustrating an ultrasonic probe 100a in accordance with another embodiment of the present invention. When comparing FIGS. 1 and 7, a support member 180a may be formed with a first area in which the sectional size of a cavity Cl is constant. Since the light emitting element 170 is disposed higher than the transducer 120 with respect to the sound absorbing member 140, advancement of light emitted from the light emitting element 170 toward the transducer 120 can be reduced.

Figure 8:
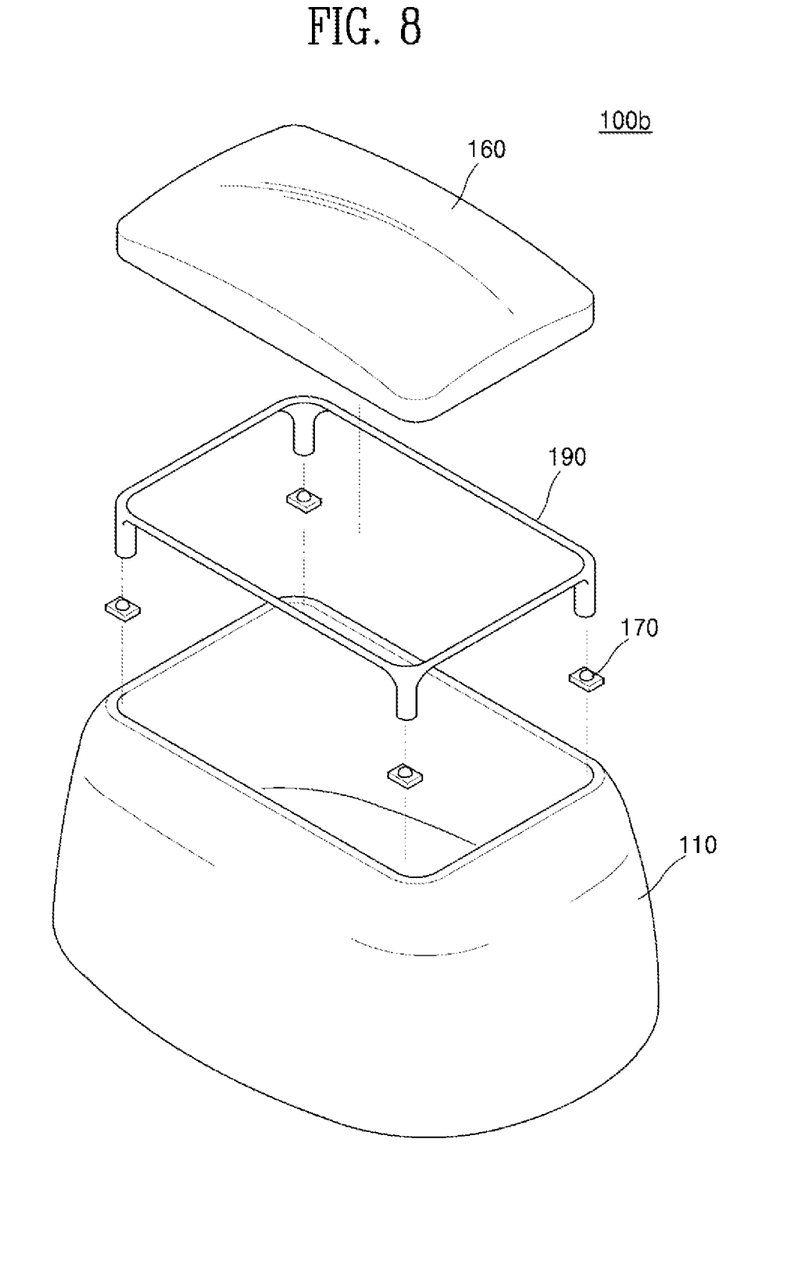
FIG. 8 is a view illustrating an ultrasonic probe in accordance with still another embodiment of the present invention.

FIG. 8 is a view illustrating an ultrasonic probe 100b in accordance with still another embodiment of the present invention. As shown in FIG. 8, the ultrasonic probe 100b may further include a light guide 190 which guides emitted from the light emitting element 170, in addition to the light emitting element 170. The light emitting element 170 may be disposed inside the case 110, and the light guide 190 may be disposed between the acoustic lens 160 and the case 110.

In addition, an area of the light guide 190, which faces the surface of the acoustic lens 160, may be formed of a transmissive material, and the other area may be formed of a reflective material. Thus, light emitted from the light emitting element 170 can advance toward the external surface of the acoustic lens 160 while passing through the light guide 190.

Figure 9:
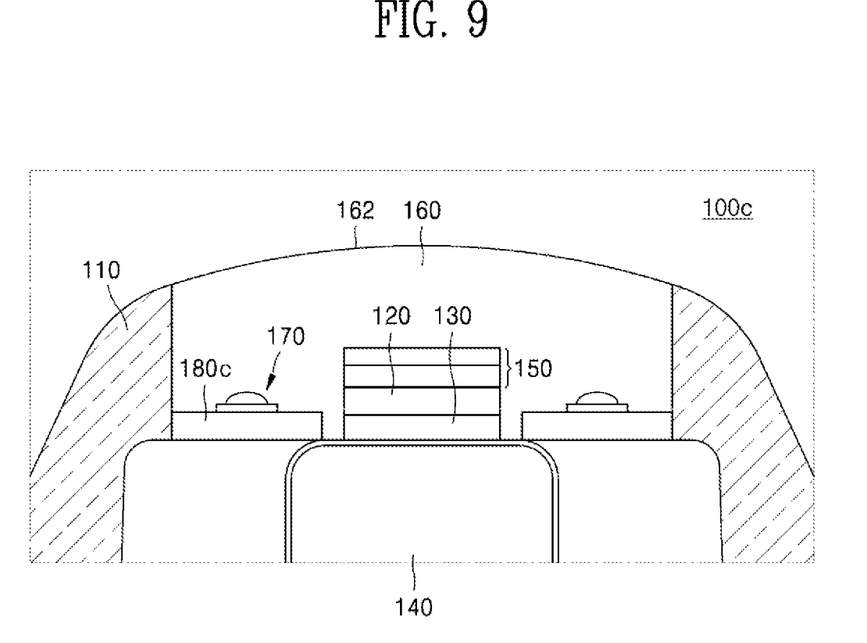
FIG. 9 is a view illustrating an ultrasonic probe in accordance with still another embodiment of the present invention.

FIG. 9 is a view illustrating an ultrasonic probe 100c in accordance with still another embodiment of the present invention. As shown in FIG. 9, the light emitting element 170 may be disposed such that the advancing path of light and the advancing path of an ultrasonic wave are parallel to each other. A support member 180c may have a shape protruding toward the transducer 120 from the case 110. In addition, the light emitting element 170 may be disposed on the above-described support member 180. The light emitting element 170 may be disposed at a position having the same height as the transducer 120 or be disposed at a position higher than the transducer 120 with respect to the sound absorbing member 140. Thus, although light is emitted from the light emitting element 170, advancement of the light toward the transducer 120 can be reduced.

Although a case where the support member 180 is a separate component of the case 110 has been described till now, the present invention is not limited thereto. The support member 180 which supports the light emitting element 170 may be integrated with the case 110, and the case 110 itself may become the support member 180.

Figure 10:
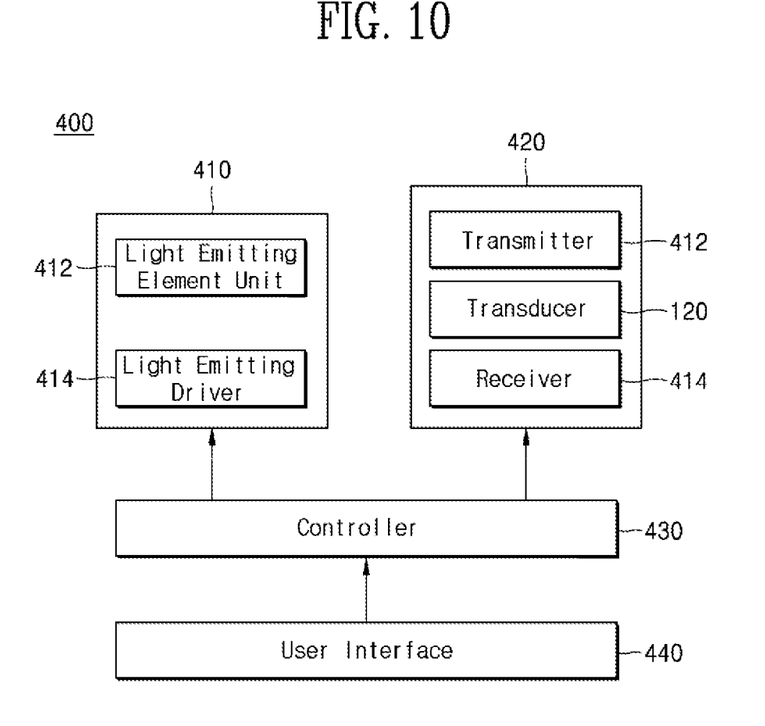
FIG. 10 is a block diagram illustrating an ultrasonic probe having a sterilizing function in accordance with an embodiment of the present invention.

FIG. 10 is a block diagram illustrating an ultrasonic probe 400 having a sterilizing function in accordance with an embodiment of the present invention. As shown in FIG. 10, the ultrasonic probe 400 may include a sterilizing module 410, an ultrasonic module 420, a controller 430, and a user interface 440. The appearance of the ultrasonic probe 400 may be the ultrasonic probe 100, 100a, 100b or 100c described above.

The sterilizing module 410 may include a light emitting element unit 412 which emits light for sterilization and a light emitting driver 414 which drives the above-described light emitting element unit 412 under the control of the controller 430.

The light emitting element unit 412 may include one or more light emitting elements 170 which emit ultraviolet light for sterilization, and be disposed inside the ultrasonic probe 100 as described above. The light emitting element 170 is disposed to be in contact with the acoustic lens 160, and light passing through the acoustic lens 160 sterilizes the external surface 162 of the acoustic lens 160. The light emitting element 170 may be disposed more distant from the central axis of the ultrasonic probe 100 than the transducer 120, and be disposed not overlap with the advancing path of the ultrasonic wave released from the transducer 120. The arrangement relationship of the light emitting element 170 has been described above, and therefore, detailed descriptions will be omitted.

The ultrasonic module 420 may include a transmitter 412, a transducer 120, and a receiver 414.

The transmitter 412 supplies a driving signal to the transducer 120. Specifically, the transmitter 412 may generate a rate pulse for forming a transmission ultrasonic wave according to a PRF (Pulse Repetition Frequency), apply a delay time for determining transmission directionality to the rate pulse, and apply a driving signal (or driving pulse) to the transducer at a timing corresponding to each rate pulse to which the delay time is applied.

The transducer 120 transmits an ultrasonic wave to a subject 10 according to the driving signal supplied from the transmitter, and receives an echo signal of the ultrasonic wave reflected from the subject 10. The transducer 120 may include a plurality of unit elements which converts an electrical signal into acoustic energy (or vice versa). The transducer 120 has been described in FIG. 3, and therefore, detailed descriptions will be omitted.

The receiver 414 generates ultrasonic data by processing a signal received from the transducer 120. Specifically, the receiver 414 amplifies the signal received from the transducer 120, and analog-digital converts the amplified signal. Also, the receiver 414 may generate ultrasonic data by applying and adding a delay time for determining reception directionality to the digital-converted signal.

The controller 430 may selectively control the ultrasonic module 420 or the sterilizing module 410 according to a certain protocol or a signal received from the user interface 440. The controller 430 may control the sterilizing module 410 to be operated in a state in which the ultrasonic module 420 is inactivated. For example, when a user command for a sterilizing operation is received through the user interface 440, the controller 420 may control the sterilizing module 410 such that light for sterilization is emitted. Alternatively, when a user command for an ultrasonic operation is received, the controller 430 may control the sterilizing module 410 such that light for sterilization is emitted for a certain time (e.g., within 20 seconds) and then control the ultrasonic module 420 to be operated after an operation of the sterilizing module 410 is ended. Alternatively, after an operation of the ultrasonic module 420 is completed, the controller 430 may allow the sterilizing module 410 to be operated for a certain time (e.g., within 20 seconds).

Alternatively, when the ultrasonic probe 100 mounted in the probe holder 292 shown in FIG. 1 receives a sensing signal, the controller 430 may control the sterilizing module 410 to perform a sterilizing operation. As described above, since the sterilizing module 410 is disposed in the ultrasonic probe 100, the ultrasonic probe 100 can perform the sterilizing operation while not transmitting/receiving an ultrasonic wave.

While the ultrasonic module 420 necessarily includes the transducer 120, at least a partial component of the transmitter 412 and 414 may be included in another apparatus. The controller 430 and the user interface 440 may also be disposed in the ultrasonic probe 100 or be implemented as a separate apparatus.

In the above, the embodiments of the ultrasonic probe have been described. While the detail embodiments of the present invention have been described, the scope of the present invention is not limited to the above-described embodiments, and various modifications and improvements of those skilled in the art that utilize the basic concept of the present invention that are defined in the following claims are also included in the scope of the invention.

The invention claimed is:

1. An ultrasonic probe comprising:
   a case;
   a transducer arranged in the case, the transducer converting electrical signals into ultrasonic waves;
   an acoustic lens arranged on the transducer, the acoustic lens causing the ultrasonic waves to converge in one area of a subject;
   a plurality of light emitting elements arranged in the case, the plurality of light emitting elements emitting light to sterilize an external surface of the acoustic lens; and
   a support member arranged in the case, the support member supporting the plurality of light emitting elements,
   wherein the support member includes: a first area overlapping with the transducer; and a second area supporting the plurality of light emitting elements, and
   wherein the second area is inclined with respect to the first area.

2. The ultrasonic probe of claim 1, wherein at least one of the plurality of light emitting elements is in direct contact with the acoustic lens.

3. The ultrasonic probe of claim 1, wherein at least one of the plurality of light emitting elements is covered by the acoustic lens.

4. The ultrasonic probe of claim 1, wherein the light sterilizes the external surface of the acoustic lens while being transmitted through the acoustic lens.

5. The ultrasonic probe of claim 1, wherein at least one of the plurality of light emitting elements emits light of a UV-C wavelength.

6. The ultrasonic probe of claim 1, wherein at least one of the plurality of light emitting elements is arranged more distant from a central axis of the ultrasonic probe than the transducer.

7. The ultrasonic probe of claim 1, wherein the plurality of light emitting elements are symmetrically arranged with respect to a central axis of the ultrasonic probe.

8. The ultrasonic probe of claim 7, wherein, in the second area, the size of a cavity becomes larger as becoming more distant from the first area.

9. The ultrasonic probe of claim 8, wherein the acoustic lens includes at least one of PDMS (polydimethyl siloxane), octamethylcyclotetra siloxane, flurorine-polymer, a silicon material, RTV (Room Temperature Vulcanizing), silicon rubber, and polyurethane.

10. The ultrasonic probe of claim 1, wherein the acoustic lens is formed of a material having a transmission of the light, which is 50% or more.

11. The ultrasonic probe of claim 1, wherein the plurality of light emitting elements are arranged on an area not overlapping with an advancing path of the ultrasonic waves inside the case.

12. The ultrasonic probe of claim 1, wherein the plurality of light emitting elements emit the light in a state in which the transducer is inactivated.

* * * * *